(12) United States Patent
Yao

(10) Patent No.: US 10,463,229 B2
(45) Date of Patent: Nov. 5, 2019

(54) ENDOSCOPIC OBSERVATION METHOD AND COMPOSITION FOR IMPROVING DIAGNOSTIC PERFORMANCE INVOLVING APPLYING USEFUL WHITE OPAQUE SUBSTANCE TO DIAGNOSIS OF GASTRIC EPITHELIAL TUMORS (ADENOMA OR GASTRIC CANCER)

(75) Inventor: Kenshi Yao, Fukuoka (JP)

(73) Assignee: FUKUOKA UNIVERSITY, Fukuoka (JP)

( * ) Notice: Subject to any disclaimer, the term of this patent is extended or adjusted under 35 U.S.C. 154(b) by 1567 days.

(21) Appl. No.: 13/880,784

(22) PCT Filed: Sep. 20, 2011

(86) PCT No.: PCT/JP2011/071389
§ 371 (c)(1),
(2), (4) Date: Apr. 22, 2013

(87) PCT Pub. No.: WO2012/053306
PCT Pub. Date: Apr. 26, 2012

(65) Prior Publication Data
US 2013/0211195 A1    Aug. 15, 2013

Related U.S. Application Data

(60) Provisional application No. 61/405,962, filed on Oct. 22, 2010.

(51) Int. Cl.
| | |
|---|---|
| *A61B 1/00* | (2006.01) |
| *A61K 49/00* | (2006.01) |
| *A61K 51/04* | (2006.01) |
| *A61K 45/06* | (2006.01) |
| *A61K 31/201* | (2006.01) |
| *A61K 31/575* | (2006.01) |
| *A61K 31/685* | (2006.01) |

(52) U.S. Cl.
CPC ............ *A61B 1/00* (2013.01); *A61K 31/201* (2013.01); *A61K 31/575* (2013.01); *A61K 31/685* (2013.01); *A61K 45/06* (2013.01); *A61K 49/0004* (2013.01); *A61K 49/0052* (2013.01); *A61K 51/0404* (2013.01)

(58) Field of Classification Search
CPC ............ A61K 49/0052; A61K 51/0404; A61K 49/0004; A61K 45/06; A61K 31/201; A61K 31/575; A61K 31/685; A61K 2300/00; A61B 1/00
See application file for complete search history.

(56) References Cited

U.S. PATENT DOCUMENTS

| | | | |
|---|---|---|---|
| 2002/0012680 A1* | 1/2002 | Patel ................... | A61K 9/4808 424/400 |
| 2010/0284929 A1* | 11/2010 | Pinchuk ............. | A61K 49/0021 424/9.6 |

OTHER PUBLICATIONS

Yao et al., Gastrointestinal Endoscopy, 2008, 68(3), p. 575-580.*
Ohtsu et al., Endosc Int Open, 2015; 03: p. E318-E322.*
Cohn et al., Nutrients, 2010, 2, p. 116-127 (Year: 2010).*

* cited by examiner

*Primary Examiner* — Michael G. Hartley
*Assistant Examiner* — Leah H Schlientz
(74) *Attorney, Agent, or Firm* — Rankin, Hill & Clark LLP

(57) ABSTRACT

To develop a clinically useful composition and an endoscopic observation method that utilizes WOS properties. The composition for improving diagnostic performance, containing lipids as a component is characterized in that, by administering or loading said composition orally, by intubation or via an endoscope, the lipids are absorbed by gastric tumors, facilitating the detection of tumors and qualitative diagnoses by endoscope. Tumors are thus whitened by administering or loading this composition for improving diagnostic performance prior to endoscopic observation, making it easier to discover and qualitatively diagnose tumors by endoscopic observation.

4 Claims, 20 Drawing Sheets

ENDOSCOPIC OBSERVATION METHOD AND COMPOSITION FOR IMPROVING DIAGNOSTIC PERFORMANCE INVOLVING APPLYING USEFUL WHITE OPAQUE SUBSTANCE TO DIAGNOSIS OF GASTRIC EPITHELIAL TUMORS (ADENOMA OR GASTRIC CANCER)

CROSS-REFERENCE TO RELATED APPLICATIONS

The present application claims priority to U.S. Provisional Application No. 61/405,962 filed on Oct. 22, 2010, herein incorporated by reference in its entirety.

TECHNICAL FIELD6

The present invention relates to an endoscopic examination method and a lipid composition for improving diagnostic performance by applying a white opaque substance to diagnosis of gastric neoplasia.

BACKGROUND TECHNOLOGY

Gastric cancer is the disease with the second cause of cancer death worldwide (Non-Patent Literature Document No. 1). In order to improve the prognosis of patients with gastric cancer and to ensure the quality of life (QOL) of the patients, the early detection of the gastric cancer is most important.

One of the reasons is because when the gastric neoplasia can be detected and treated at its early stage, it may be treated with a high degree of complete recovery.

As another reason, if the gastric cancer could be detected at a very early stage without its spreading to lymph nodes or other organs, a lesion may be resected by an endoscope while the gastric function is preserved. The endoscopic therapy for such an early gastric neoplasia may achieve a therapeutic outcome equivalent to the surgery, and patients may maintain the QOL at a level similar to that before the therapy.

Patients with early gastric cancer have usually no subjective symptoms of the neoplasia. Therefore, in order to make the early detection of the gastric cancer, a screening test by diagnostic imaging is generally recommended.

Among various diagnostic imaging methods, the gastroscopy (endoscopy in the stomach) is the most useful examination method for efficiently detecting early neoplasia because it allows a detection of subtle mucosal changes in color and surface pattern, which may be caused in the development of the early gastric neoplasia.

In addition, when a lesion can be detected by gastroscopy as being suspected as neoplasia, a specimen may be collected from the lesion by a biopsy using forceps through the endoscope, leading to a definitive histopathological diagnosis of the biopsy specimen.

From those advantages as described above, the gastroscopy is placed to be the most efficient examination for the early detection of gastric neoplasia.

In recent years, with the advancement of technology, a zoom endoscope that can magnify its optical observation up to eighty times was developed and applied in clinical practice.

The inventors have developed a technique to observe capillaries of the stomach by using the zoom endoscope (Non-Patent Literature Document No. 2) and detected a microvascular architecture that is characteristic of early gastric neoplasia (Non-Patent Literature Document No. 3). They have also applied these findings clinically to a screening examination for early gastric neoplasia and reported that these findings are useful for making an accurate diagnosis of the smaller and flat neoplasia (Non-Patent Literature Document No. 4). The present findings and the present zoom endoscopy technique are clinically applied not only in Japan but also widely around the world.

Furthermore, as a result of the observation by a zoom endoscope, the inventors have found that a lesion in the stomach may contain a white substance that does not transmit projected light into the epithelium of gastric epithelial neoplasia (adenoma or carcinoma) and that this white substance may disturb the observation of a subepithelial microvascular architecture that works as a marker of the diagnosis of the early gastric neoplasia. The nature, origin, and the like of this white substance was then unknown, therefore, the inventors named and reported the white substance as a white opaque substance (WOS) (Non-Patent Literature Document No. 5).

Recently, in addition to the zoom endoscope described above, an image-enhanced endoscopy such as a narrow-band imaging (NBI) has been developed. A combination of such an image-enhanced endoscopy technique with a zoom endoscope can allow a more clear observation of the structure of the epithelium, blood vessels and the like on the mucosal surface.

In the case when the endoscopic observation of the subepithelial microvessels was disturbed by the WOS in a lesion, an analysis of the morphological features of the WOS was carried out in combination of the NBI with a zoom endoscope (a NBI-combined magnifying endoscopy). As a result, it has been found that the WOS found in neoplastic lesions showed an irregular morphology, while that found in non-neoplastic lesions showed a regular morphology. Based on these findings, the present inventors have reported that the WOS could be a marker useful for the differential diagnosis between cancerous lesions and non-cancerous lesions (Non-Patent Literature Document Nos. 5 and 6).

Although the morphological features of the WOS became clear for making a histological diagnosis, the nature and origin of the WOS still remains unclear. In addition, a WOS can be recognized only in 50% of gastric epithelial neoplasia (adenoma or carcinoma). Therefore, it has been considered to be less feasible for clinical application of the WOS.

CITATION REFERENCE LISTING

Non-Patent Literature Document No. 1: Ferlay. Int J Neoplasia 2010

Non-Patent Literature Document No. 2: Yao K, Oishi T. Dig Endosc 2001; 13: S27-S33

Non-Patent Literature Document No. 3: Yao K, Oishi T, MatsuiT, et al. Gastrointest Endosc 2002; 56: p. 279-284

Non-Patent Literature Document No. 4: Yao K, Iwashita A, Tanabe H, et al. Clini Gastroenterol Hepatol 2007; 5: p. 869-878

Non-Patent Literature Document No. 5: Yao K, Iwashita A, Tanabe H, et al. Gastrointest Endosc 2008; 68: p. 574-580

Non-Patent Literature Document No. 6: Written and Edited by Kenshi Yao, "Gastric Magnifying Endoscopy (the First Edition)", Nihon Medical Center, Inc., published on May 28, 2009

SUMMARY OF THE INVENTION

According to the background described above, an object of the present invention is to clarify the nature and origin of a WOS and further to develop a clinically useful composition and an endoscopic examination method by utilizing the nature of the WOS.

As a result of extensive studies, the inventors have found that the WOS comprises lipid droplets.

This finding has not been conceivable from the ordinary common technical knowledge because the stomach is an organ that usually retains and digests food, but never absorbs nutrients such as lipid. Therefore, even if the cells in the normal stomach would be mutated to neoplastic cells, it cannot be usually considered to become feasible that the neoplastic cells originated from the stomach could accumulate a lipid. However, on the contrary, the inventors have found that the WOS comprises minute lipid droplets (fat droplets) accumulated within the epithelial cells of gastric neoplasia (adenoma and carcinoma).

From the above findings, the inventors assumed that the lipid droplets accumulated in the gastric neoplasia would be derived from an exogenous fat contained in meals since the lipid droplets are not present in normal gastric epithelial cells. Accordingly, the inventors carried out the immunohistochemical staining for a tissue sample of the gastric neoplasia performed and then, they proved that the stomach may acquire a phenotype like the intestine that can absorb a lipid, if the gastric epithelial cells would be mutated to neoplastic cells. Thus, the inventors came to the conclusion that the WOS is derived from an exogenous lipid. More specifically, the exogenous lipid in meals is digested in the stomach, and the digested exogenous lipid is not absorbed in normal gastric epithelial cells, but in the gastric neoplasia that has acquired a lipid absorptive capacity. The lipid absorbed in the gastric neoplasia may be accumulated in the gastric neoplasia and constitute lipid droplets, and then the lipid droplets can be observed as a WOS by endoscopy.

Based on these findings, the inventors further performed an endoscopic examination for patients who suffer from a gastric epithelial neoplasia, but who had not been confirmed to have a WOS within the gastric epithelial lesions in the previous endoscopic examination. The endoscopic examination was carried out after giving the patients a fat-enriched food that is likely to be absorbed in the gastric epithelial neoplastic tissue. The test results revealed that a whitening of gastric neoplasia was confirmed by an ordinary endoscopic observation (a non-magnifying endoscopy) and an accumulation of the WOS in the gastric epithelium neoplasia was also detected on the same neoplasia using zoom gastroscopy. Based on these findings, the present invention has been completed regarding a composition for improving diagnostic performance and an endoscopic observation method, which enables endoscopists to clearly distinguish gastric neoplasia from normal tissue by lipid loading.

The present invention consists of the following aspects.

The first aspect of the present invention is directed to a composition for improving diagnostic performance, comprising a lipid as a component, wherein the lipid is absorbed into gastric neoplasia by administering or loading the composition orally, intraluminally by a tube or via an endoscope, thereby permitting an easy detection and a qualitative diagnosis of neoplasia by an endoscope.

The second aspect of the present invention is involved with the composition for improving diagnostic performance described in the first aspect, wherein the lipid is selected from one or more than one of simple lipid compound lipid, and derived lipid.

The third aspect of the present invention is involved with the composition for improving diagnostic performance described in the first or second aspect, wherein the composition for improving diagnostic performance is in liquid form.

The fourth aspect of the present invention is involved with the composition for improving diagnostic performance described in the third aspect, wherein the lipid forms micelles.

The fifth aspect of the present invention is involved with the composition for improving diagnostic performance described in the fourth aspect, wherein the micelles are composed of bile acid, a monoglyceride, a fatty acid, a phospholipid, and a sterol.

The sixth aspect of the present invention is involved with the composition for improving diagnostic performance described in the fifth aspect, wherein the monoglyceride is contained in the ratio of from 0.2 to 0.6 by weight, the fatty acid is contained in the ratio of from 0.2 to 0.6 by weight, the phospholipid is contained in the ratio of from 0.01 to 0.5 by weight, and the sterol is contained in the ratio of from 0.01 to 0.1 by weight, respectively, with respect to the bile acid.

The seventh aspect of the present invention is involved with the composition for improving diagnostic performance described in the first to sixth aspects, wherein the lipid is chemically modified by one or more than one of the group selected from a fluorescent-labeling functional group, a functional dye group, an ultraviolet-absorbing functional group, and a radionuclide.

The eighth aspect of the present invention is involved with an endoscopic examination method, wherein the lipid is absorbed into gastric neoplasia of a subject by administering or loading the composition for improving diagnostic performance described in the first to seventh aspects orally, intraluminally by a tube or via an endoscope, thereby permitting an easy detection and a qualitative diagnosis of neoplasia by an endoscope.

Further, in the present invention, the terms "lipid forms micelles" are intended to mean a state in which micelles are formed by lipid molecules themselves or a lipid is dissolved in the hydrophobic region of a micelle.

Advantageous Effects of the Invention

The composition and the endoscopic examination method for improving diagnostic performance of the present invention provide a clinically useful composition and examination method.

More specifically, the administration or loading of the composition for improving diagnostic performance according to the present invention prior to endoscopic examination can increase the density of the WOS in gastric neoplasia, thereby improving a contrast of the gastric neoplastic cells against the background mucosal epithelium and permitting an easy detection of the gastric neoplasia. In addition, the morphological analysis of the WOS in the gastric neoplasia visualized by NBI-combined magnifying endoscopy becomes easy when the density of the WOS is increased. As a result, the composition for improving diagnostic performance and the endoscopic examination method of the present invention can easily allow an easy detection and qualitative diagnosis of gastric neoplasia by endoscopic examination.

MODES FOR CARRYING OUT THE INVENTION

Figure 1:
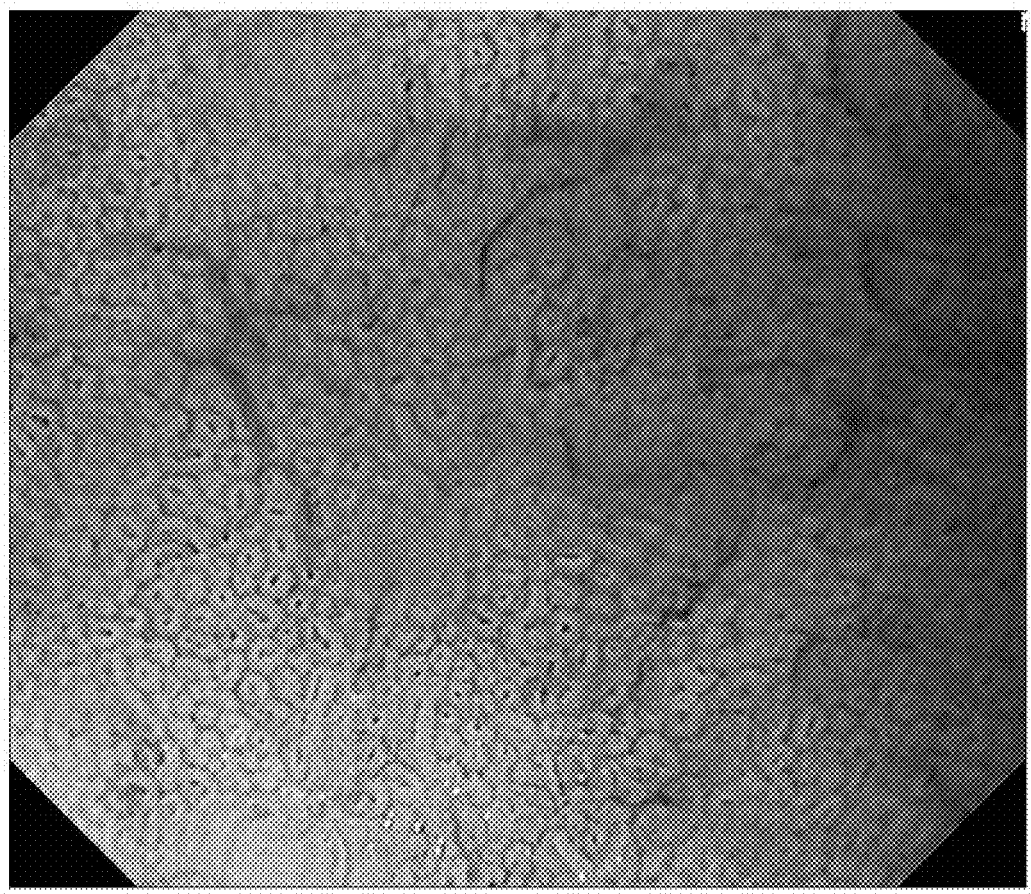
FIG. 1 shows a NBI-combined magnifying endoscopic image of normal gastric corpus.

A description will be made hereinafter regarding the composition for improving diagnostic performance and endoscopic examination method according to the present invention.

The composition for improving diagnostic performance according to the present invention may contain a lipid as an essential component. The composition for improving diagnostic performance of the present invention may be formulated by single lipid molecules or multiple lipid molecules. The composition may also contain the lipid in an appropriate amount and ratio by taking its properties and dosage form, the dose and loading amount to subjects and the like into consideration.

The composition for improving diagnostic performance of the present invention may also be constituted as a food such as "lactoice" (ice cream with milk-solids content of 3% or greater) or as medicine. The composition of the present invention may contain various additives.

The lipid in the composition according to the present invention may be defined herein as a lipophilic molecule whose molecule itself or whose degradation products produced in vivo by gastric acid or lipase can be absorbed through the gastrointestinal epithelium. For example, a triglyceride may not be usually absorbed in the gastrointestinal epithelium in an unchanged molecular form, however, it may be degraded by gastric acid or pancreatic lipase converting to a monoglyceride, followed by forming micelles with bile acid and being absorbed in the gastrointestinal epithelium. Therefore, the triglyceride may be included in the lipid since the in vivo degradation products can be absorbed through the gastrointestinal epithelium. Hereinafter, unless otherwise mentioned in particular, the lipophilic molecule is used as the term that includes a molecule itself and its degradation products produced in vivo by gastric acid, lipase or the like.

Lipid is not required to be limited to a particular one as long as its lipophilic molecule can be absorbed through the gastrointestinal epithelium. Examples of the lipids may include, for example, a simple lipid, a compound lipid and a derived lipid, and these lipids may be used singly or in combination with plurals. Furthermore, one or plurals of the simple lipids may be used, and the same is applied to the other lipids.

Simple lipid may be defined herein as a lipophilic molecule that is composed of carbon atoms, hydrogen atoms, and oxygen atoms. The simple lipid in the narrow meaning may include a fatty acid ester molecule in which an alcohol, a glycerol, a cholesterol or the like is bound to a fatty acid. Examples of this simple lipid may include, for example, a triglyceride, a diglyceride, a monoglyceride, a fatty acid alkyl ester and a cholesterol ester of a fatty acid.

The fatty acid constituting the simple lipid is not required to be limited to a particular one as long as the lipophilic molecule can be absorbed in the gastrointestinal epithelium, and various fatty acids can be used. As the fatty acid, there may be used, for example, a saturated fatty acid and an unsaturated fatty acid. The saturated fatty acid may include, for example, lauric acid, myristic acid, palmitic acid, stearic acid, arachidic acid, and the like. The unsaturated fatty acid may include, for example, palmitoleic acid, oleic acid, linoleic acid, γ-linolenic acid, arachidonic acid, α-linolenic acid, eicosapentaenoic acid, docosahexaenoic acid, and the like.

The alcohol constituting the simple lipid is not limited to a particular one as long as its lipophilic molecule can be absorbed in the gastrointestinal epithelium, and there may be used an alcohol with an appropriate carbon chain length in combination with a fatty acid. Examples of the alcohol may include, for example, ethanol, propanol, butanol, isobutyl alcohol, benzyl alcohol and the like.

The cholesterol constituting the simple lipid is not limited to a particular one as long as its lipophilic molecule can be absorbed in the gastrointestinal epithelium, and an appropriate cholesterol can be selected in combination with a fatty acid. Examples of the cholesterols may include, for example, cholesterol, β-sitosterol, campesterol, stigmasterol, brassicasterol, ergosterol and the like.

Compound lipid may be defined as a lipophilic molecule which may contain atoms other than carbon atoms, hydrogen atoms, and oxygen atoms (phosphorus, sulfur or nitrogen) or polar molecules such as sugars. The simple lipid is a molecule in which phosphoric acid, sugar, choline, amino acid or the like is bound to an ester of a fatty acids or a glycerol. As the compound lipid, there may be mentioned, for example, a phospholipid, a sphingolipid, a glycolipid, and the like.

Examples of the phospholipids may include, for example, phosphatidic acid, bisphosphatidic acid, lecithin (soy lecithin, egg yolk lecithin, lysolecithin and the like), cephalin, phosphatidyl ethanolamine, phosphatidyl methyl ethanolamine, phosphatidyl serine, phosphatidyl inositol, phosphatidyl glycerin, diphosphatidyl glycerin, and the like.

Examples of the sphingolipids may include, for example, sphingomyelin, sphingoethanolamine, cerebroside, ceramide, sphingosine, phytosphingosine, and the like.

Examples of the glycolipid may include, for example, glucocerebroside, galactocerebroside, ganglioside, and the like.

Derived lipid may be defined herein as a molecule that may be produced by hydrolysis of the simple lipid or the compound lipid or as a sterol (a molecule having a sterol backbone). As the derived lipids, there may be mentioned, for example, a long-chain fatty acid, cholesterols, bile acids (cholic acid, desoxycholic acid, glycocholic acid, taurocholic acid, hyocholic acid, shiburinol, deoxycholic acid, lithocholic acid, hyodeoxycholic acid, ursodeoxycholic acid, and the like), and lipophilic vitamins.

The lipophilic molecule may be chemically modified as long as its absorptive capacity to the gastrointestinal epithelium is not impaired.

As the chemical modifications, there may be used, for example, fluorescent modifications (modifications by a fluorescent-labeling functional group) by a porphyrin-related compound. When an endoscope system equipped with a fluorescence detection capability is used, not only a whitening of gastric neoplasia but also fluorescence from the gastric neoplasia can be detected, enabling an easy detection and qualitative diagnosis of gastric neoplasia.

Similarly, modifications by dyes including, for example, indigo carmine, methylene blue and the like (modifications by a dye functional group), modifications by a functional group having a large ultraviolet absorptivity such as a benzyl group (modifications by an ultraviolet absorbing functional group), modifications by a radionuclide such as $^{99m}$Tc, and the like can be performed for the purpose of improving diagnostic performance of the composition according to the present invention.

The chemical modification method may be selected appropriately depending on the functional group to be modified. For example, a compound can be synthesized in which a straight-chained alkyl group having an amino group or a carboxyl group is introduced into a porphyrin ring (a fluorescent-labeling functional group), a phenothiazine ring of methylene blue (a dye functional group), or the like. There may also be used compounds, such as tyrosine or phenylalanine (a compound having an ultraviolet-absorbing functional group) or $^{99m}$Tc-DTPA (a compound having a radionuclide), which have an amino group or a carboxyl group. The amino group or the carboxyl group of these compounds may be bound to an alcohol group of the monoglyceride or a carboxyl group of the fatty acid.

As described above, although the lipid in the composition for improving diagnostic performance of the present invention is not required to be particularly limited as long as the lipophilic molecule is absorbed through the gastrointestinal epithelium, it is preferred to use the molecule in which the lipid itself or the degradation product (particularly the degradation product produced by the degradation by gastric acid or lipase) does not exert pharmacological effects. This can suppress demonstration of the pharmacological effects due to the fact that the lipid or its degradation product to be digested or absorbed from other than the gastric neoplasia is consumed simply as energy or utilized as a component for structuring the human body, etc., leading to an improvement in the safety for administration of the composition for improving diagnostic performance to the human body.

The lipid may be chemically synthesized or extracted from animals, plants or the like. For example, a triglyceride as the simple lipid can be extracted from the fat and oil of animals or plants, and lecithin, which is one phospholipid of the compound lipid, can be extracted from egg yolk, plants, or the like.

The composition for improving diagnostic performance of the present invention can be selected from various properties and dosage forms, such as solid, semisolid, liquid, and so on, however, a liquid form is most preferred. This can assist in easily administering or loading the composition of the present invention orally, intraluminally by a tube, or via an endoscope, thereby enhancing the effect for improving the convenience of use of the composition for improving diagnostic performance. In addition, the composition for improving diagnostic performance can be loaded directly onto gastric neoplasia under endoscopic observation, enhancing the effect for improving the diagnostic performance. As a method for making the composition into a liquid form, there may be used various methods for making suspension, emulsion, and the like.

Further, the composition for improving diagnostic performance of the present invention is preferably used as the emulsion in which the lipid is in the form of a micelle. The lipid in the micelle form can be made in a state close to the state in which the lipid can be absorbed physiologically, thereby enhancing the effect that the lipid can be easily absorbed in the gastric neoplasia. It is to be noted herein that the terms "lipid forms micelles" mean a state in which the micelles are formed by lipid molecules themselves, or a state in which the lipid is dissolved in the hydrophobic regions of the micelles, or both.

Although the lipid may be formed into a micelle body by various methods, it is preferred to use, for example, a method of using am amphipathic lipid for the lipid or a method of adding an emulsifier to the composition of the present invention.

The amphipathic lipid to be used herein may be defined as the lipid that has hydrophilic and hydrophobic groups in one molecule and that is not dissolved in water.

As the amphipathic lipid, there may be mentioned, for example, a higher fatty acid, a higher alcohol, a sphingolipid, a glycolipid, a phospholipid, and a structural analog thereof.

Examples of the long-chain fatty acid may include, for example, myristic acid, stearic acid, oleic acid, palmitic acid, and behenic acid.

Examples of the higher alcohol may include, for example, octanol, myristyl alcohol, cetyl alcohol, cetostearyl alcohol, stearyl alcohol, behenyl alcohol, isostearyl alcohol, chimyl alcohol, batyl alcohol, and selachyl alcohol.

Examples of the sphingolipid may include, for example, ceramide, and phytosphingosine.

Examples of the glycolipid may include, for example, glucocerebroside, galactocerebroside, and ganglioside.

Examples of the phospholipid may include, for example, phosphatidic acid, bisphosphatidic acid, lecithin (soy lecithin, egg yolk lecithin, lysolecithin, and the like), cephalin, phosphatidyl ethanolamine, phosphatidyl methyl ethanolamine, phosphatidyl serine, phosphatidyl inositol, phosphatidyl glycerin, and diphosphatidyl glycerin.

The amphipathic lipid may be used alone or in combination with two or more. The mixing ratio of the amphipathic lipid can be appropriately selected and adjusted from the various viewpoints of the kind and number of the amphipathic lipid to be selected, additives and the like. Further, the amphipathic lipid has a function as an emulsifier or a surfactant in a manner as will be described later, however, the emulsifier, etc. and the amphipathic lipid are not needed to be considered separately for the composition of the present invention, and the amphipathic lipid can be used as a lipophilic molecule having multiple functions.

Further, as the emulsifier to be used for forming micelles, an appropriate emulsifier may be selected depending on the lipid that works as a component of the composition. As the emulsifiers, there may be mentioned, for example, an ionic surfactant and a non-ionic surfactant. The non-ionic surfactant is preferred from the viewpoint of the safety to the human body.

The ionic surfactants may include, for example, an alkyl sulfate, a polyoxyethylene alkyl ether sulfate, a polyoxyethylene alkyl ether acetate, an alkyl trimethyl ammonium chloride, an alkoxy propyl trimethyl ammonium chloride, a dialkyl dimethyl ammonium chloride, an alkyl dimethylamino acetic acid betaine, an alkyl dimethyl amine oxide, and the like.

The non-ionic surfactants may include, for example, a glycerin fatty acid ester, an organic acid monoglyceride, a propylene glycol fatty acid ester, a polyglycerin condensed ricinoleic acid ester, a sorbitan fatty acid ester, a polyoxyethylene sorbitan fatty acid ester, polysorbate, a bile acid, and the like.

As such a composition of the micelle body, there may be mentioned, for example, a 1 L micellar solution (25 µM, phosphate buffer, pH 7.0, containing, as lipid, 2.8 g of oleic acid, 1.28 g of safflower monoglyceride, and 8.5 g of sodium taurocholate).

As a more preferable embodiment of the micelle body in the present invention, there may be mentioned, for example, an emulsion composed of bile acid (containing bile salt), monoglyceride, fatty acid, phospholipid, and sterols. This emulsion can make the lipid in a state closer to a physiologically absorptive state and produce the effect for facilitating the lipid absorption in gastric neoplasia. The composition of the micellar body can be made in a state close to a composition present in vivo by adjusting the monoglyceride in the weight ratio of 0.2 to 0.6, the fatty acid in the weight ratio of 0.2 to 0.6, the phospholipid in the weight ratio of 0.01 to 0.5, and the sterols in the weight ratio of 0.01 to 0.1, based on weight of the bile acid.

The composition containing such a micellar body can be produced, for example, by the following procedures. First, 2.0 g of bovine bile acid, 920 mg of cholesterol, and 135 mg of lysophosphatidylcholine are added in this order to 75 mL of phosphate buffer (150 mM, pH 7.0) and dissolved, followed by addition of 700 mg of monooleic acid, and 700 mg of oleic acid. After mixing, phosphate buffer is added to obtain a total volume of 100 mL. While this phosphate buffer solution is stirred, sonication is performed at room temperature. The obtained emulsion and micellar solution are further stirred, and then ultrasonic separation is performed at 100,000×g, 25° C. for 16 to 18 hours. After the ultrasonic separation, only the transparent micellar layer is collected to yield a solution containing micelle bodies.

In addition to the emulsifier described above, the composition for improving diagnostic performance of the present invention may contain various additives as a component, including, for example, an excipient, a lubricant, a binder, a disintegrant, a solvent, a solubilizing agent, a suspending agent, an isotonic agent, and a buffering agent. A preservative, an antioxidant, and a sweetener can also be used.

The following is a description regarding the endoscopic examination method according to the present invention.

The endoscopic observation method of the present invention may be performed in accordance with an endoscopic examination method that is usually performed, except for administering or loading the composition for improving diagnostic performance of the present invention prior to or during the endoscopic examination. More specifically, a subject undergoes an endoscopic examination after fasting from the previous night of the endoscopic observation and subjecting to pretreatment with a medical solution for removing the gastric mucosa.

In the endoscopic examination method according to the present invention, the composition for improving diagnostic performance containing a lipid as one of the components is administered to or loaded on a subject prior to or during the endoscopic examination.

As a specific example, the composition for improving diagnostic performance of the present invention is administered to or loaded on a subject undergoing the endoscopic observation 4 to 16 hours before the endoscopic examination. The endoscopic examination may be usually carried out after subjects have undergone a conventional pre-treatment prior to the insertion of an endoscope.

As another embodiment, when the composition for improving diagnostic performance according to the present invention is in a liquid form as containing a lipid in the form of a micellar body, the endoscopic examination may be performed by administering or loading the composition by directly injecting it into the lesion through the forceps opening of the endoscope during the endoscopic examination, followed by washing it with physiological saline or the like.

The endoscopic examination method according to the present invention may increase a WOS density in the gastric neoplasia to a higher rate as compared with the gastric neoplasia in which a WOS can be observed at the rate of only around 50% or with the gastric neoplasia in which, even if the WOS can be observed, it is still difficult to be distinguished clearly from the gastric neoplastic lesions due to the fact that the accumulation of the WOS is less. This can improve a contrast of the gastric neoplastic lesions against the mucosal epithelium as a background, making a detection of the gastric neoplasia easier. In addition, the gastric neoplasia with the increased density of WOS can allow an easy analysis of the morphology of the WOS by NBI-combined magnifying endoscopic examination. The morphology of the WOS can provide information useful for qualitative diagnosis, i.e., for example, when the morphology of the WOS within a neoplastic lesion is regular such as symmetrical, on the one hand, it is highly possible that the lesion is of a type of a benign neoplasia, and when the morphology thereof is irregular such as asymmetrical, on the other hand, it is highly possible that the lesion is of a type of a malignant neoplasia. As a result of the above, the endoscopic examination method according to the present invention can lead to a very easy detection and qualitative diagnosis of gastric neoplasia.

EXAMPLES

The present invention will be described in detail hereinafter, however, as a matter of course, the content of the present invention is not at all considered as being limited to the following contents.

<Endoscopic Examination Protocol>

The following is a description regarding a standard protocol of the endoscopic examination, which is performed in the following Examples.

All subjects who underwent the endoscopic examination in the following Examples were examined after giving their written informed consent in advance. In the Examples, patients who were receiving warfarin and another anticoagulant treatment as well as subjects who did not give informed consent were excluded from the examination. It is to be noted that the endoscopic examinations in the following Examples were carried out for all the subjects by an experienced skilled endoscopist who are familiar with this procedure.

1. All the subjects received the following composition 30 minutes prior to the endoscopic observation in order to remove the mucus from the gastric surface.

Composition: water 100 mL, pronase 20000 unit, sodium bicarbonate 1 g, and dimethylpolysiloxane (20 mg/mL) 10 mL.

2. After the insertion of the endoscope, the endoscopic observation was performed after washing the targeted site or a peripheral area surrounding it with 20 mL of water through the endoscope and removing the mucus therefrom in the event when the mucus is strongly adhered to the targeted site or to the peripheral area thereof.

3. The following devices were used for the endoscopic observation. An ordinary non-magnifying observation and magnifying observation as well as a magnifying observation with NBI were performed in combination with the following devices. In addition, the endoscopist operating the endoscope can easily change the magnification of the endoscope and an observation light such as white light and narrow-band light by the lever or button equipped in the handle part of the endoscope.

Universal upper-gastrointestinal (GIF-Q240Z, Olympus, or GIF-H260Z, Olympus); and Endoscopic videoscope system (Evis Lucera Spectrum, Olympus).

4. Before the insertion of the endoscope, the endoscopist attached a black soft hood to the tip of the endoscope and performed the endoscopic observation. The black soft hood can allow the endoscopist to always maintain a distance of 3 mm between the tip of the endoscope zoom lens and the tissue surface. The distance of 3 mm is the distance equal to the focal length at the time when the lens captures the enlarged observation target upon the endoscopic observation at the maximum magnification. This enables the maximally enlarged endoscopic image by a magnifying endoscope.

5. If a mucosal lesion was detected by the ordinary non-magnifying endoscopic observation using white light, the hood attached to the tip of the endoscope was immediately brought into contact with the mucosal surface to perform a magnifying observation and NBI-combined magnifying endoscopy. Further, the biopsy was performed to collect a sample from the center of the lesion under non-magnifying observation.

6. When the endoscopic observation is performed, images were taken and stored in the following four cases. Together with the above, the biopsy specimens were collected and pathological definitive diagnosis was performed for the biopsied specimens. The results of the definitive diagnosis and each morphology were compared and examined.

(1) WOS is present or not;

(2) When WOS is present, the morphology of a WOS (whether a regular arrangement or irregular arrangement);

(3) Subepithelial microvascular architecture is visible or not; and (4) Morphology of microvessels (the microvascular architecture is regular or irregular).

7. As a comparative example, NBI-combined magnifying endoscopic images of the normal parts are shown in FIGS. 1 and 2.

(1) FIG. 1 shows a NBI-combined magnifying endoscopic image of normal gastric corpus. In this image, no WOS was detected, but a capillary network and collecting venules were identified.

Figure 2:
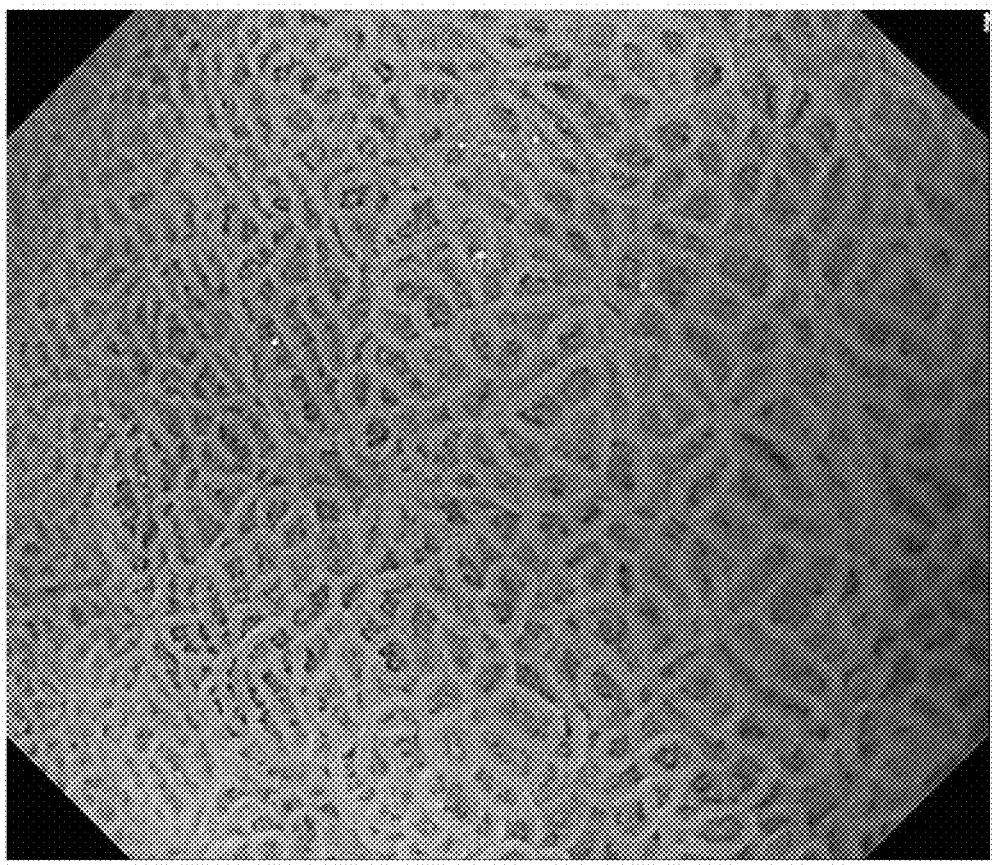
FIG. 2 shows a NBI-combined magnifying endoscopic image of normal gastric antrum.

(2) FIG. 2 shows a NBI-combined magnifying endoscopic image of normal gastric antrum. Although no WOS was detected, the capillary network was identified.

Example 1

Confirmation of the Nature of WOS

Example 1 was performed for the purpose of confirming whether or not the lipid droplets are the nature of the WOS.

<Method>

1. Example 1 was carried out for 28 early gastric epithelial neoplasias from 24 patients who gave written informed consent.

2. By NBI-combined magnifying endoscopic examination, the presence or absence of the WOS was examined in a neoplastic lesion and a mucous epithelium around the neoplastic lesion (hereinafter referred to as "surrounding mucosa" in the Example).

3. After the NBI-combined magnifying endoscopic observation was finished, one biopsy specimen was collected from each of the neoplastic lesion and the surrounding mucosa thereof, and the biopsy specimens were immediately frozen.

4. The frozen specimens obtained above were subjected to histopathological examination. Specifically, the frozen sections of the specimens were subjected to lipid staining (oil-red O staining) to examine the presence or absence of fat droplets in the neoplastic specimens. The histopathological examination was performed for a total of 58 specimens (28 neoplastic specimens and 28 non-neoplastic specimens) from 24 subjects.

<Results and Discussion>

The NBI-combined magnifying endoscopic examination revealed that, among 58 sites from which the biopsy specimens were collected, the WOS was detected in 19 sites and no WOS was identified in the remaining 39 sites (Table 1). Among the 19 sites where the WOS was detected, the presence of fat droplets (FD) was confirmed in the 18 sites (for example, FIGS. 12, 15, and 18). Further, among 39 sites where the WOS were not identified, no presence of fat droplets (FD) was confirmed in the biopsy specimens (for example, FIG. 20). These results confirm that the presence or absence of the WOS is strongly correlated with the presence or absence of fat droplets and that the nature of the WOS is minute fat droplets accumulated in the epithelial neoplasia.

TABLE 1

The prevalence of WOS by ME with NBI
and FDs in the specimens (n = 58)

|  |  | WOS | | | |
|---|---|---|---|---|---|
|  |  | Positive (n = 19) | | Negative (n = 39) | |
| FDs | Positive | 18 | (31.0%) | 1 | (1.7%) |
|  | Negative | 1 | (1.7%) | 38 | (65.7%) |

ME: magnifying endoscopy; NBI: narrow-band imaging; WOS: white opaque substance
The presence of WOS is remarkably dependent upon the presence of the FDs($p < 0.0001$, Fisher's exact test)

Example 2

Examination of Correlation Between WOS and Gastric Neoplasia of Specific Phenotype In the event where WOS is present in gastric neoplasia, correlation between the WOS and a specific phenotype of gastric neoplasia was examined.
<Method>
1. Example 2 was performed using 49 lesions of early gastric epithelial neoplasia lesions from 43 subjects with early gastric epithelial neoplasia from whom written informed consents were obtained.
2. By NBI-combined magnifying endoscopic examination using only neoplasia as the target, the presence or absence of the WOS was examined.
3. After the NBI-combined magnifying endoscopic observation, one biopsy specimen was collected from each neoplasia and immediately frozen.
4. After making the frozen sections of the frozen specimens obtained above, first, the presence or absence of fat droplets in the neoplastic tissue was examined using fat staining (oil-red O staining). Second, 6 serial sections were subjected to immunohistochemical staining by using MUC2, CDX2, CD10, MUC5AC, HGM and MUC6 as a primary antibody. Tissue phenotypes were classified into the following three types.
  (1) Intestinal phenotype (I): when the specimen is positive for either one of MUC2, CDX2, and CD10.
  (2) Gastric phenotype (G): when the specimen is positive for either one of MUC5AC, HGM, and MUC6.
  (3) Gastrointestinal phenotype (GI): when the specimen showed both phenotypes
5. For a total of 49 biopsy specimens collected from 49 neoplasias of 43 patients, the above pathological investigations was performed.
<Results>
1. The NBI-combined magnifying endoscopic examination revealed that, among 49 sites of the biopsy specimens collected from the gastric epithelial neoplasias, WOS were present in the 26 sites and WOS were absent in the remaining 23 sites (Table 2). Further, the presence of fat droplets (FD) was confirmed in the biopsy specimens obtained from 25 sites out of 26 sites where WOS were present (for example, FIGS. 12, 15, and 18). In addition, it could be confirmed that at droplets were absent in the biopsy specimens obtained from 22 sites out of 23 sites where WOS were absent. As a result, it could be confirmed also in Example 2 like in Example 1 that the presence of WOS is strongly correlated with the presence of fat droplets and that the nature of the WOS is minute fat droplets accumulated in the neoplastic epithelium.

2. The biopsy specimens collected from gastric neoplasias in which the WOS were confirmed were composed of 0 specimen of G type, 13 specimens of GI type, and 13 specimens of I type, respectively. Namely, a WOS was not present in G type, while the WOS was present only in GI type and I type (Table 3). The results of the above examination strongly suggested that the WOS can be present in a gastric neoplasia that acquired an intestinal phenotype even among the gastric neoplasias.

3. The histological localization of fat droplets revealed that, among 26 biopsy specimens in which the WOS were confirmed, the presence of the fat droplets was confirmed in the intraepithelium only in 10 biopsy specimens and it was confirmed in both of the intraepithelium and the subepithelium in 16 biopsy specimens (Table 4).

TABLE 2

Histological prevalence of FDs by oil red O staining according to the presence of WOS by ME with NBI.

|  |  | WOS | | | |
|---|---|---|---|---|---|
|  |  | Positive (n = 26) | | Negative (n = 23) | |
| FDs | Positive | 25 | (96.2%) | 1 | (4.3%) |
|  | Negative | 1 | (3.8%) | 22 | (95.7%) |

TABLE 3

Phenotypic characterization according to the presence of the WOS

|  |  | WOS | | | |
|---|---|---|---|---|---|
|  |  | Positive (n = 26) | | Negative (n = 23) | |
| Phenotype | G | 0 | (96.2%) | 11 | (47.8%) |
|  | GI | 13 | (50%) | 4 | (17.4%) |
|  | I | 13 | (50%) | 8 | (34.8%) |

WOS: white opaque substance; G: gastric phenotype; GI: gastrointestinal phenotype; I: intestinal phenotype

TABLE 4

Histrogical distribution of FDs (n = 26)

| Distribution | Number of lesions | |
|---|---|---|
| Intraepithelial | 10 | 38.5% |
| Intraepithelial + subepithelial | 16 | 61.5% |
| Subepithelial | 0 | 0% |

Example 3

Comparison of NBI-Combined Magnifying Endoscopic Examinations in Subjects with Gastric Neoplasia (Adenoma) to Whom Fat Food was Loaded Subjects in whom no WOS was observed in the gastric neoplasia by endoscopic observation were subjected to the following examination. After they ingested fat food, the endoscopic observation was performed to examine whether a WOS can be observed in the gastric neoplasia or not.
<Method>
1. The ordinary endoscopic observation was carried out for the subjects who ingested no fat food, and they were examined 10 days thereafter by endoscopy by taking a commercially available fat food twice 16 hours and 4 hours prior to the endoscopic observation. p Overview of the Fat Food:

(1) Product classification: "lactoice" (ice cream with milk-solids content of 3% or greater)

(2) Product weight (volume): 177 g (190 mL)

(3) Nutritional composition:

Energy: 241 kcal

Protein: 3.3 g

Fat: 12.6 g

Carbohydrate: 29.1 g

Sodium: 82 mg

Non-fat milk solids: 5%, vegetable fat: 7%, and egg fat: 0.2%

(4) Names of raw materials:

Sugar, dairy products, vegetable oil, fructose, egg yolk, salt, flavor, stabilizer (polysaccharide thickener), emulsifier, and annatto dye (5) Composition:

Emulsifier: glyceric acid fatty acid ester, less than 0.1%

Stabilizer: guar gum, locust bean gum and carrageenan, less than 0.1%

Dye: annatto dye, less than 0.1%

Flavor: vanilla, custard and milk, 0.2%

<Results>

1. Results are shown in FIGS. 3 to 6.

Figure 3:
FIG. 3 shows an ordinary endoscopic image of a gastric adenoma in the patient's stomach.
Figure 4:
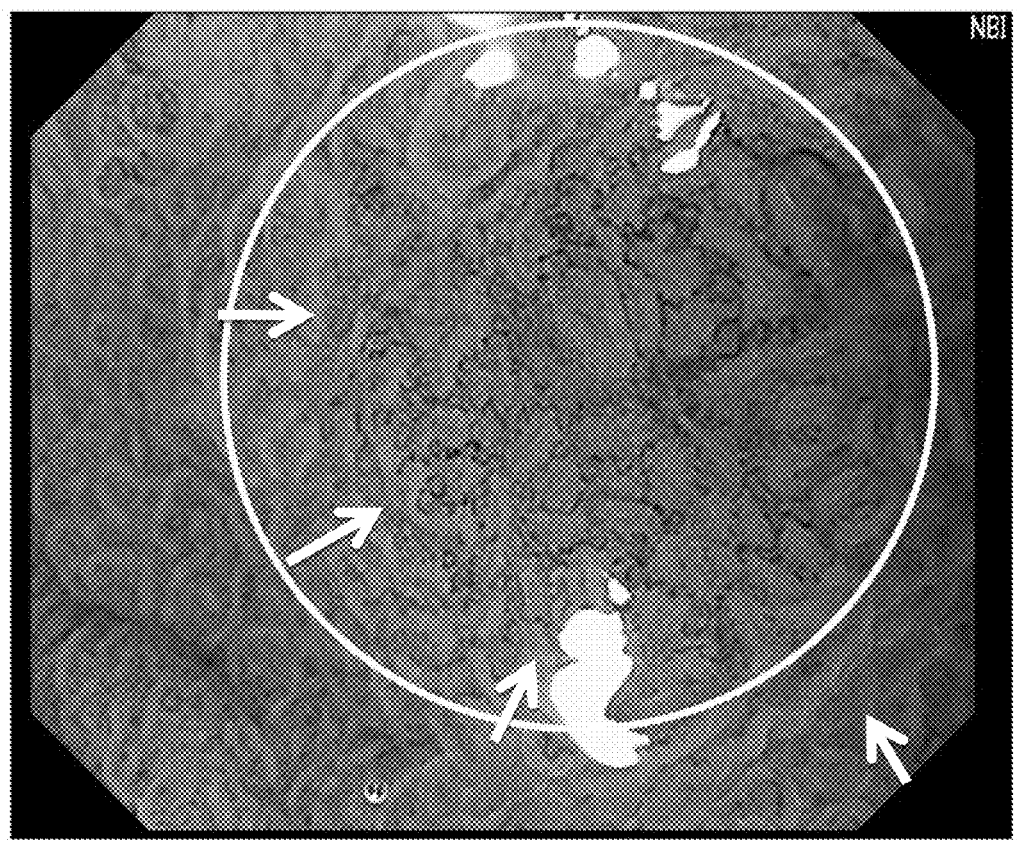
FIG. 4 shows a NBI-combined magnifying endoscopic image of a border of adenoma in the patient's stomach.

2. FIGS. 3 and 4 show images of the endoscopic observation performed prior to the ingestion of fat food. In the ordinary observation, the gastric neoplastic lesions showed a little difference in color from the surrounding mucosa so that it was difficult to identify the neoplastic lesion and the detection of the neoplastic lesion was not easy (FIG. 3). The NBI-combined magnifying endoscopy clearly confirmed a brown microvascular architecture, but no WOS was present (FIG. 4).

Figure 5:
FIG. 5 shows an ordinary endoscopic observation image after loading an adenoma patient with an ice cream (with milk-solids content of 3% or greater: "lactoice").
Figure 6:
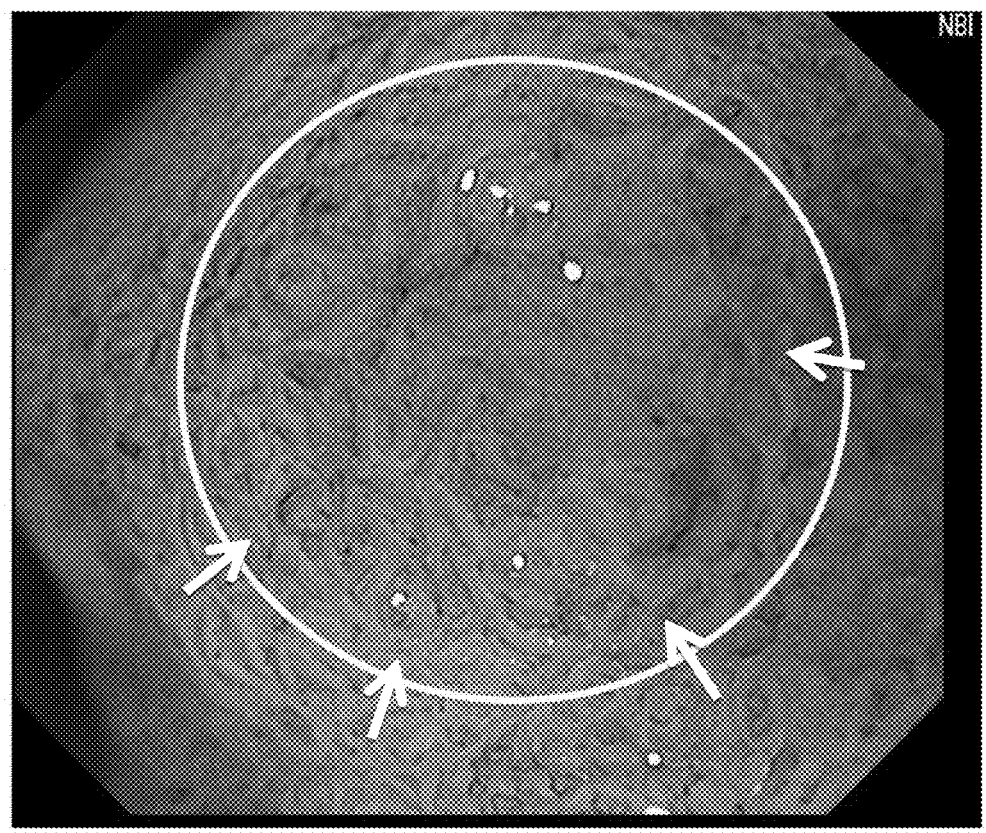
FIG. 6 shows a NBI-combined magnifying endoscopic observation image of adenoma border after loading an adenoma patient with "lactoice".

3. The ordinary observation after the ingestion of fat food shows a whitening of the lesion increasing a contrast of the neoplastic lesion against the surrounding mucosa. This was helpful to detect the neoplasia (FIG. 5). The NBI-combined magnifying endoscopy confirmed that the WOS was deposited to such a depth that the observation of the subepithelial blood vessels underneath the deposition was blocked (FIG. 6).

4. The above results revealed that, even in gastric neoplasia in which no WOS was observed, a WOS could be deposited on the gastric epithelial neoplasia by ingesting fat food prior to the endoscopic observation, thereby allowing the WOS to be observed by an endoscope.

5. As a result, if a certain condition could be set likely for a lipid to come into contact with and to be absorbed by the gastric neoplasia in order to increase a contrast of the gastric neoplastic lesion against its surrounding mucosa, a rate of detection of gastric neoplasia can be increased and a qualitative examination capability by an endoscope can also be increased by visualizing the WOS. That is, it is considered that the diagnostic performance of neoplasia by an endoscope can be improved.

Example 4

The subepithelial microvascular architecture of gastric neoplasia is known to be a means of distinguishing gastric adenoma from gastric carcinoma. In Example 4, it was examined whether the morphology of the WOS can become an index of the differential diagnosis of adenoma (non-carcinoma) and carcinoma in a similar manner as the microvascular architecture can.

<Method>

1. Example 4 was performed for 46 sites of the gastric neoplastic lesions from 42 subjects with gastric neoplasia (surface-elevated type) from whom written informed consents were obtained.

2. The NBI-combined magnifying endoscopy was carried out to observe the presence or absence and the morphology of a WOS as well as the morphology of microvascular architecture. A histopathological diagnosis was also performed using 46 biopsy specimens from 46 neoplastic lesions. The morphology of the WOS and the morphology of the microvascular architecture (microvascular pattern (MVP)) were classified, respectively, according to the following criteria.

(1) Regular WOS:

Arrangement is regular, and distribution is symmetrical.

Morphology is uniform, reticular, maze-like, macular, or punctate.

Relatively high density (2) Irregular WOS:

Arrangement is irregular, and distribution is asymmetric.

Morphology is non-uniform, reticular, macular or punctate and rich in diversity.

Relatively density is low and minute.

(3) Regular MVP:

Morphology of each microvessel is uniform and shows a regular, closed and curved loop or an open and curved loop.

Each microvessel is varied in caliber and is irregular in size.

Distribution of the microvessels is symmetric, and arrangement is regular.

(4) Irregular MVP:

Morphology of each microvessel shows a non-uniform and diversified morphology.

Each microvessel is varied in caliber and is irregular in size.

Distribution of the microvessels is asymmetric, and arrangement is irregular.

3. After the endoscopic observation, a biopsy specimen of the lesion was collected and then subjected to a histopathological evaluation.

<Results>

1. The WOS was present more in adenoma than in gastric carcinoma (Table 5).

2. All the adenomas showed a regular WOS morphology. The gastric carcinoma at the rate of 83% showed an irregular WOS morphology (Table 6).

3. The MVP was detected at a frequency lesser in adenomas than in gastric carcinoma (Table 7). The reason for the results of this examination is considered that the frequency of the presence of the WOS is higher in adenomas than in gastric carcinoma (Table 5).

4. The MVP morphology of the adenoma showed a regular MVP morphology at the rate of 86% of the adenomas, while an irregular MVP morphology at the rate of 96% of the gastric carcinoma (Table 8).

5. The above results suggest that the lesion is considered at a high probability to be an adenoma (non-carcinoma) when a regular WOS was detected, while to be a carcinoma when an irregular WOS was detected. This means that the morphology of the WOS can become an index useful for a qualitative diagnosis of gastric neoplasia.

TABLE 5

Presence of WOS according to histologic type

|  | n | Present | | Absent | |
| --- | --- | --- | --- | --- | --- |
| Adenoma | 18 | 14 | (78%) | 4 | (22%) |
| Carcinoma | 28 | 12 | (48%) | 16 | (57%) |

TABLE 6

Morphology of detected WOS according to histologic type

|  | n | Regular | | Irregular | |
| --- | --- | --- | --- | --- | --- |
| Adenoma | 14 | 14 | (100%) | 0 | (0%) |
| Carcinoma | 12 | 2 | (17%) | 10 | (83%) |

TABLE 7

Visualization of MVP according to histologic type

|  | n | Visible | | Invisible | |
| --- | --- | --- | --- | --- | --- |
| Adenoma | 18 | 7 | (89%) | 11 | (61%) |
| Carcinoma | 28 | 27 | (96%) | 1 | (4%) |

TABLE 8

Morphology of visualized MVP according to histologic type

|  | n | Regular | | Irregular | |
| --- | --- | --- | --- | --- | --- |
| Adenoma | 7 | 6 | (86%) | 1 | (14%) |
| Carcinoma | 27 | 1 | (4%) | 26 | (96%) |

Image Examples

1. The endoscopic observation images and the histopathological evaluations performed in the above examples will be explained hereinafter with reference to the drawings.

2. FIG. 1 shows a NBI-combined magnifying endoscopic image of normal gastric corpus. In the image, no WOS can be confirmed, but a capillary network and collecting venules can be confirmed.

3. FIG. 2 shows a NBI-combined magnifying endoscopic image of normal gastric antrum. No WOS can be confirmed, but the capillary network can be confirmed.

4. The endoscopic images before and after loading of fat food on a patient with adenoma were compared (Example 2).

(1) FIG. 3 shows an ordinary endoscopic image of the patient with adenoma. Although adenoma of surface-elevated type can be detected within the circle (gastric antrum) of the image, it is difficult to detect the lesion because the neoplastic lesion has the same color tone as the surrounding mucosa.

(2) FIG. 4 shows a NBI-combined magnifying endoscopic image of adenoma border area (The arrow heads indicate the borders). In the inside neoplasia area indicated by the arrows, no WOS can be confirmed, but brown microvascular architecture can be detected.

(3) FIG. 5 shows an ordinary endoscopic observation image after loading "lactoice". The image shows an adenoma so whitened that the neoplasia becomes easily detectable.

(4) FIG. 6 shows a NBI-combined magnifying endoscopic observation image of the adenoma border areas after loading "lactoice" (the arrows indicate border areas). In the inside neoplasia areas indicated by the arrows, the NBI-combined magnifying endoscopic observation confirmed that the WOS is deposited to such a high depth that the subepithelial blood vessels cannot be detected.

Figure 7:
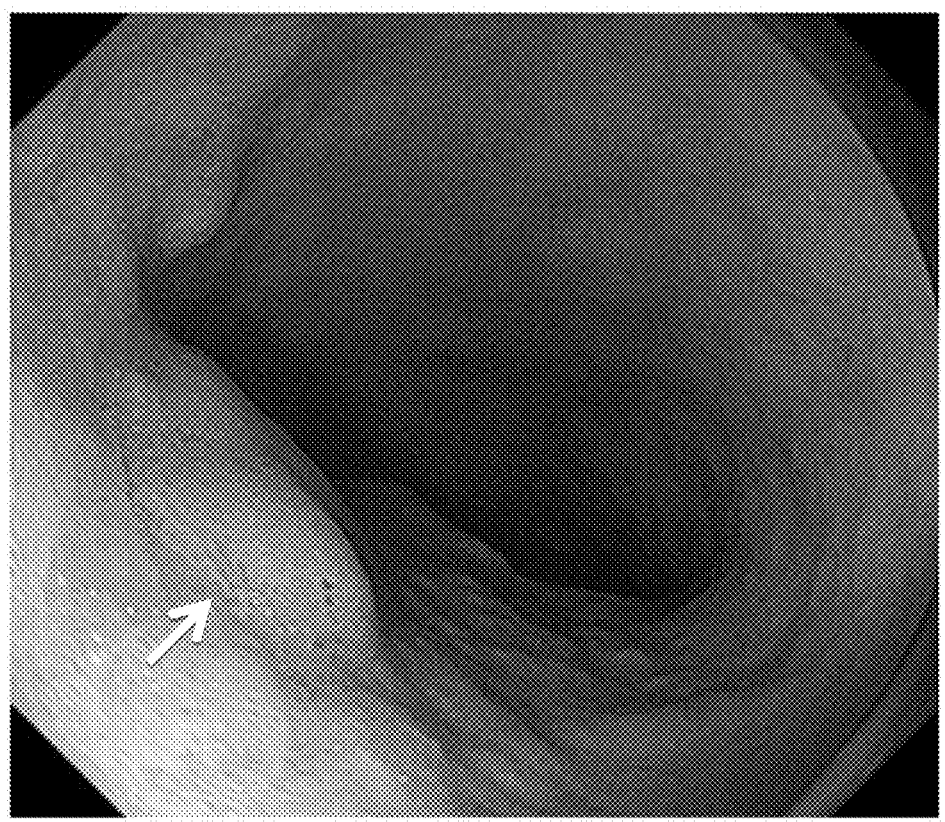
FIG. 7 shows an ordinary endoscopic observation image of adenoma in a patient with adenoma of elevated type.

5. Endoscopic image of adenoma of elevated-type (low-grade dysplasia):

(1) FIG. 7 shows an ordinary endoscopic observation image of a subject with adenoma of elevated type. The adenoma of elevated type (as indicated by the arrow head) having a white color is confirmed in the gastric antrum.

Figure 8:
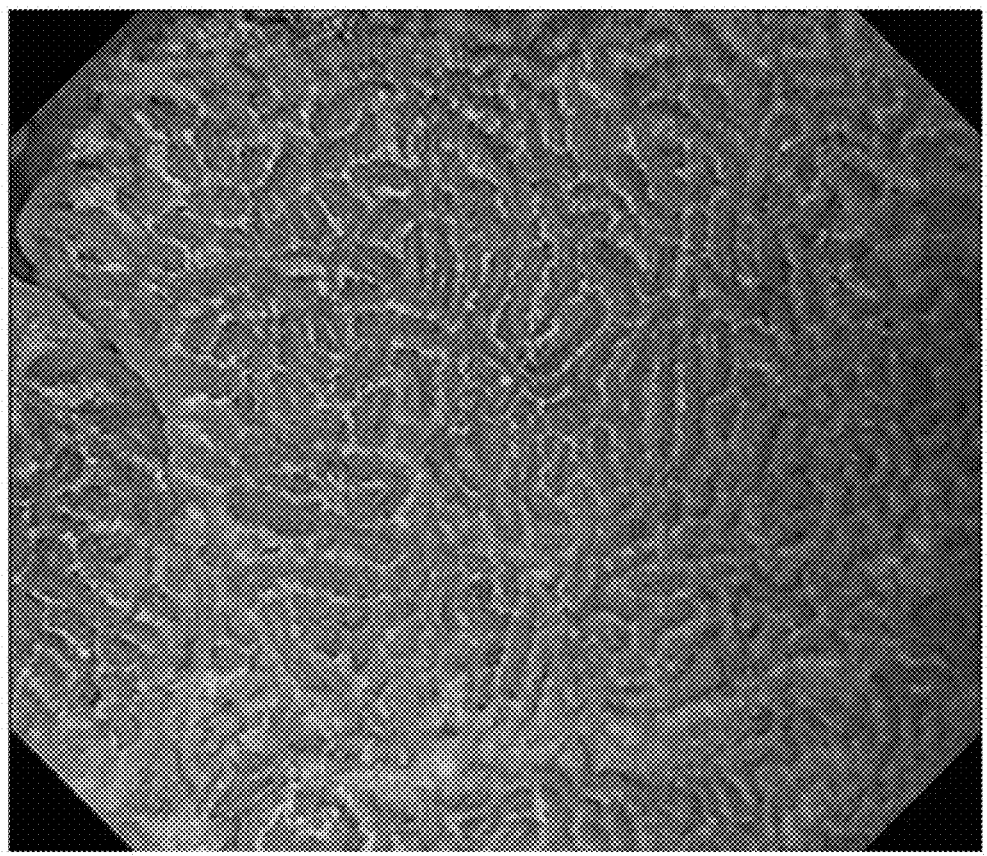
FIG. 8 shows a NBI-combined magnifying endoscopic image of adenoma part of adenoma in a patient with adenoma of elevated type.

(2) FIG. 8 shows a NBI-combined magnifying endoscopic image of adenoma part. A WOS is confirmed, and a cingulate WOS is arranged regularly in a maze-like form.

Figure 9:
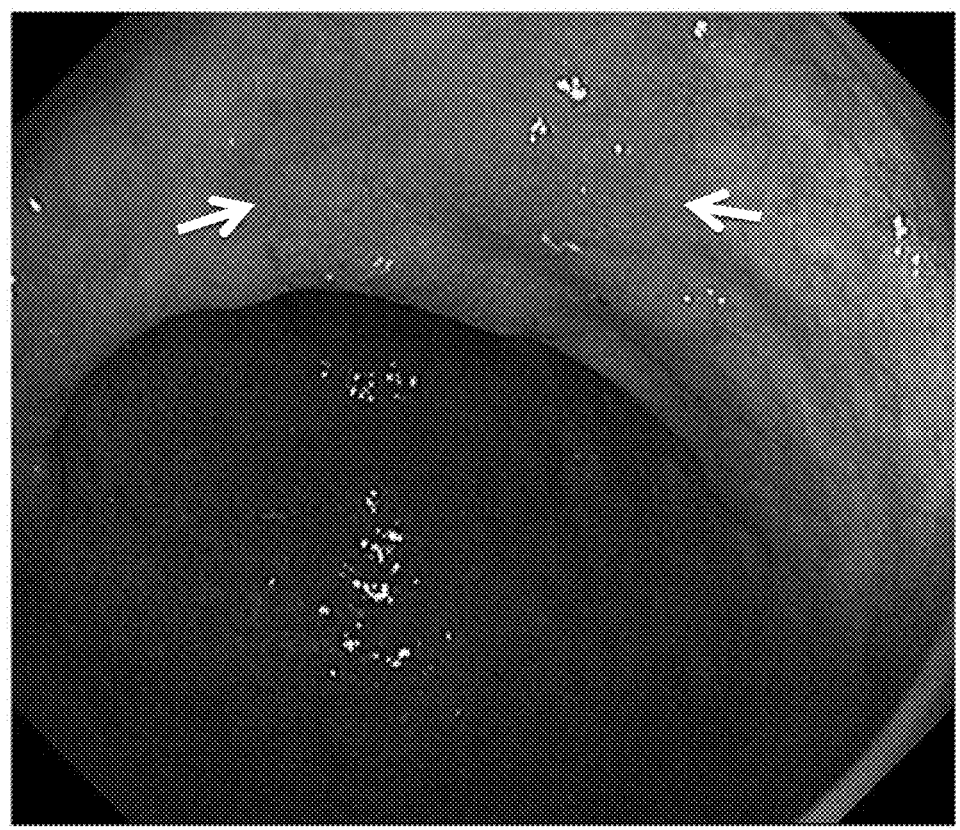
FIG. 9 shows an ordinary endoscopic image of carcinoma in a patient with gastric carcinoma of elevated type.

6. Carcinoma of elevated type (high-grade dysplasia):

(1) FIG. 9 shows an ordinary endoscopic image of a patient with carcinoma (high-grade dysplasia) of elevated type. The image shows reddened gastric carcinoma of elevated type (as shown by arrows) on a posterior wall of the gastric angle.

Figure 10:
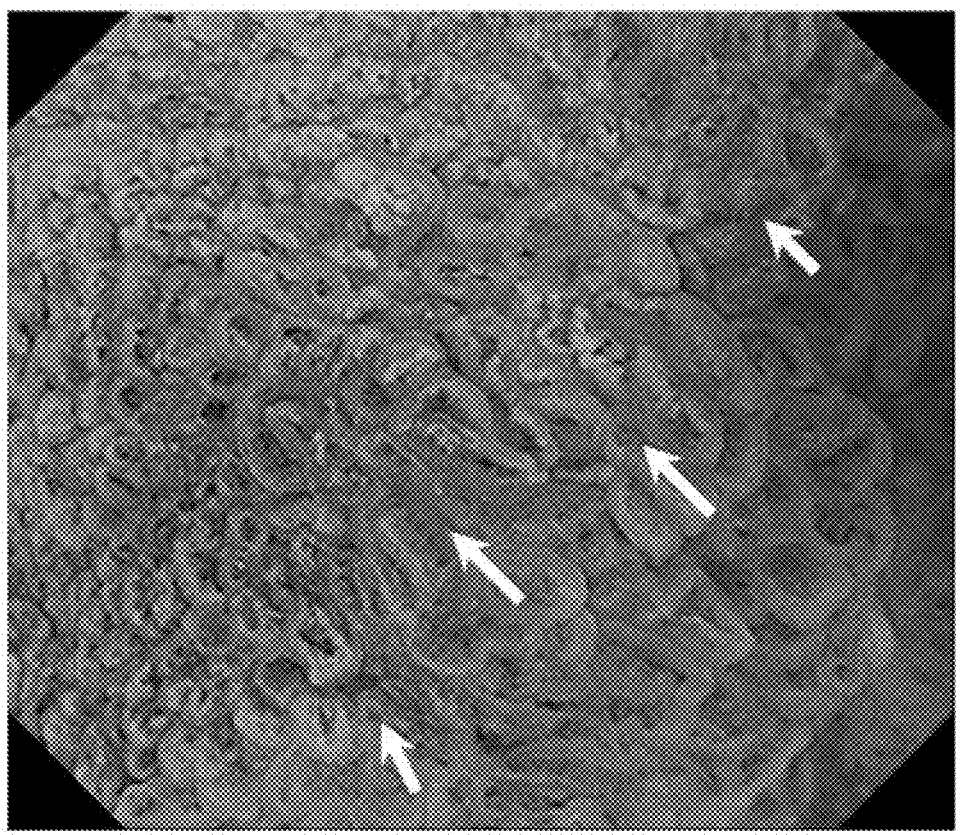
FIG. 10 shows a NBI-combined magnifying endoscopic image of gastric neoplasia border of carcinoma in a patient with gastric carcinoma of elevated type.

(2) FIG. 10 shows a NBI-combined magnifying endoscopic image of a border area of gastric carcinoma (as indicated by arrows). The WOS which shows non-uniform speckled morphology are arranged irregularly.

Figure 11:
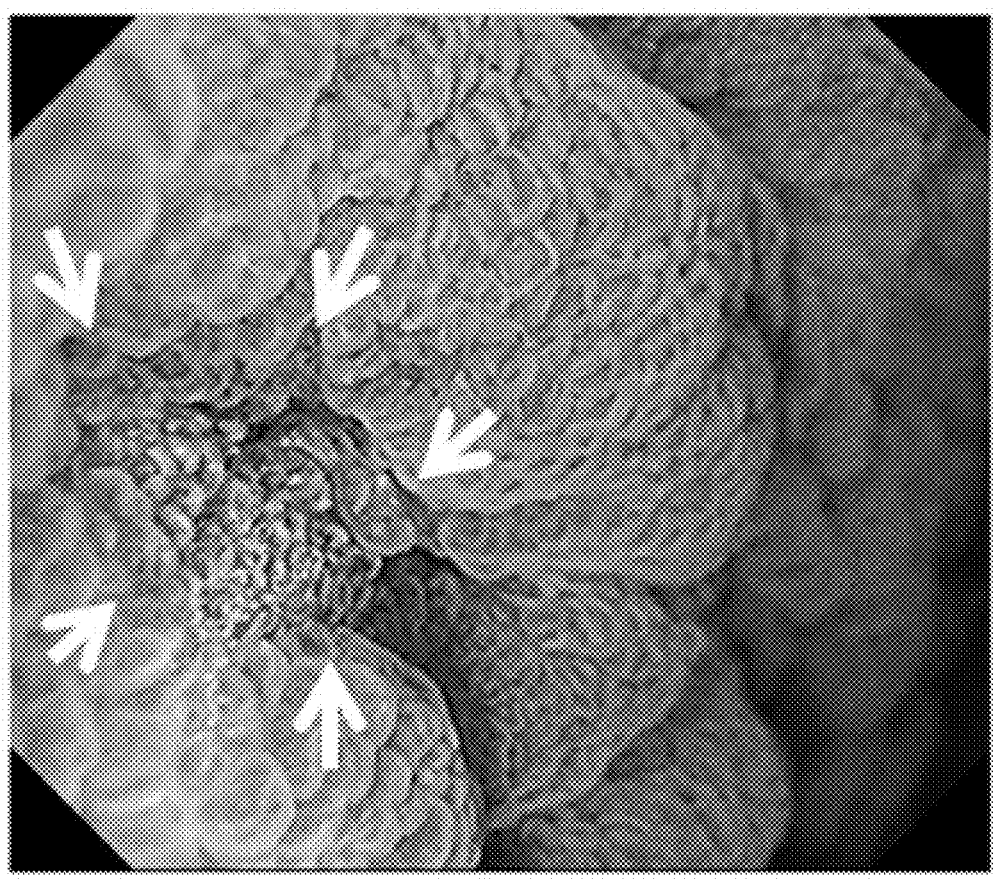
FIG. 11 shows a NBI-combined magnifying endoscopic image of carcinoma in a patient with gastric carcinoma of depressed type.

7. Subject with gastric carcinoma of depressed type:

(1) FIG. 11 shows a NBI-combined magnifying endoscopic image of gastric carcinoma of depressed type. The depressed carcinoma part inside the carcinoma border shown by arrows has an irregular arrangement of the non-uniform WOS.

Figure 12:
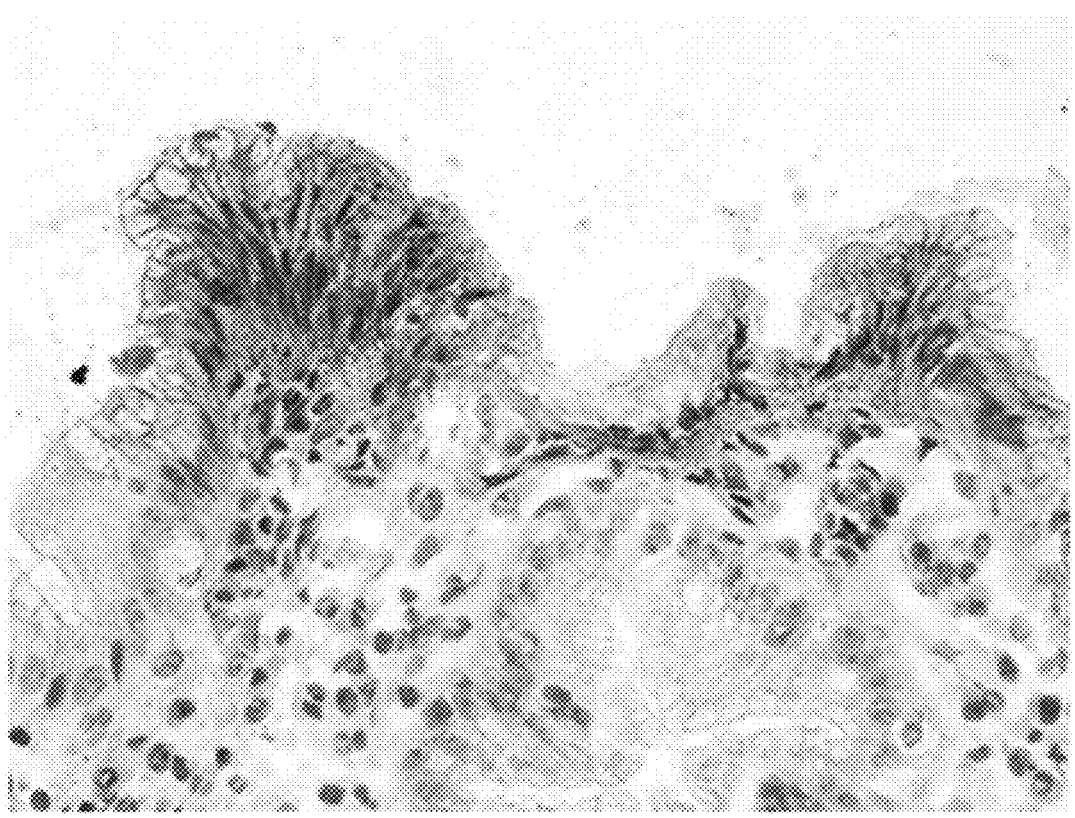
FIG. 12 shows an oil-red O (ORO) staining image of a biopsy specimen obtained from a gastric carcinoma in a patient with gastric carcinoma of depressed type.

(2) FIG. 12 shows histopathological findings (ORO staining) of a biopsy specimen collected from a gastric carcinoma part. It can be confirmed that minute fat droplets having various shapes are present in epithelial cells and lamina propria mucosae underneath the epithelium.

Figure 13:
FIG. 13 shows an ordinary endoscopic image of adenoma in a patient with adenoma of elevated type.

8. Endoscopic image and histopathological photo of adenoma of elevated type:

(1) FIG. 13 shows an ordinary endoscopic image of a subject with adenoma of elevated type. Adenoma of elevated type can be confirmed in the gastric cardia.

Figure 14:
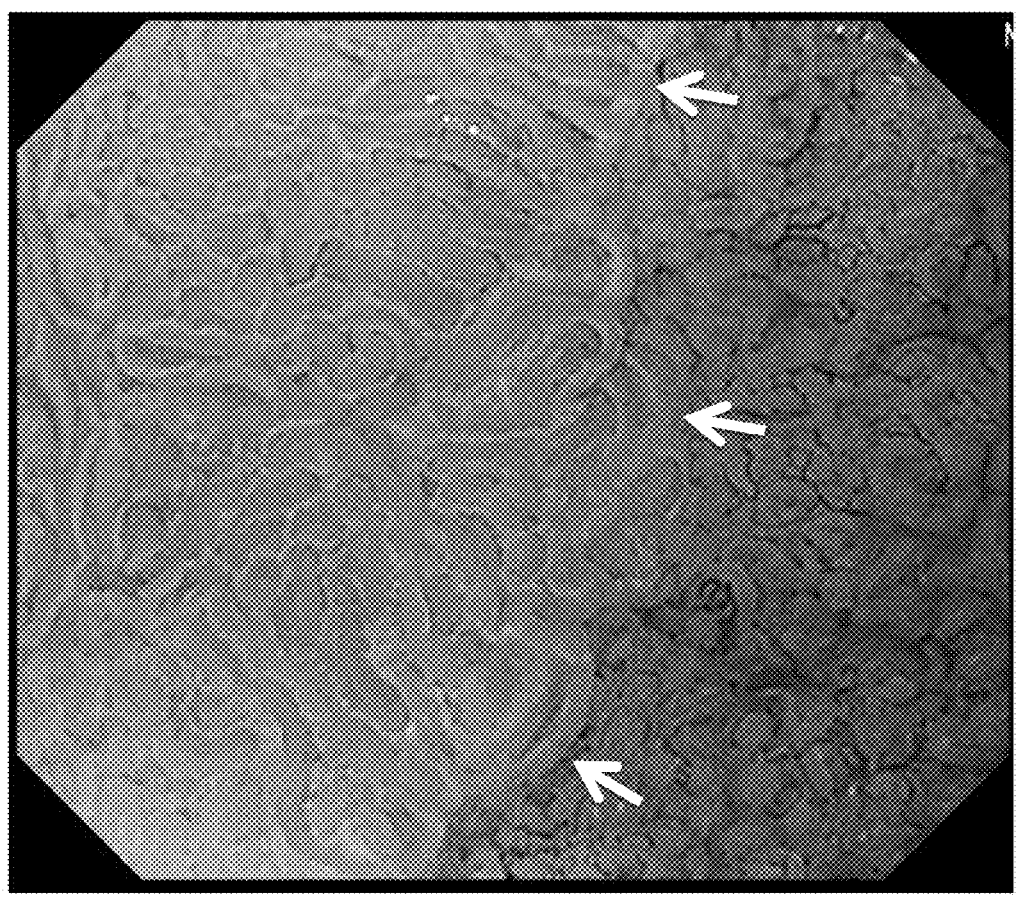
FIG. 14 shows a NBI-combined magnifying endoscopic image of a border of adenoma in a patient with adenoma of elevated type.

(2) FIG. 14 shows a NBI-combined magnifying endoscopic image of a border area of adenoma (as indicated by arrows). In the neoplasia inside the adenoma border shown by arrows, WOSs are observed in such a fashion that cingulate WOSs are regularly arranged in a maze-like form.

Figure 15:
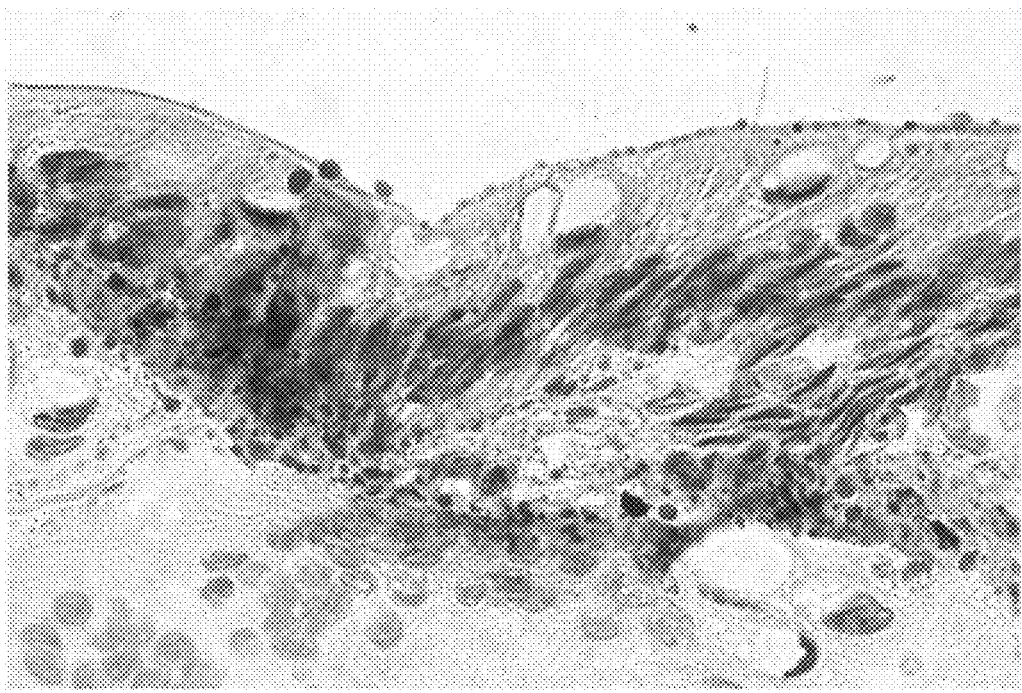
FIG. 15 shows an ORO staining image of a biopsy specimen obtained from an adenoma in a patient with adenoma of elevated type.

(3) FIG. 15 shows histopathological findings (ORO staining) of a biopsy specimen collected from adenoma. It can be confirmed that a large number of oval fat droplets are accumulated in the epithelium and the lamina propria mucosae underneath the epithelium.

Figure 16:
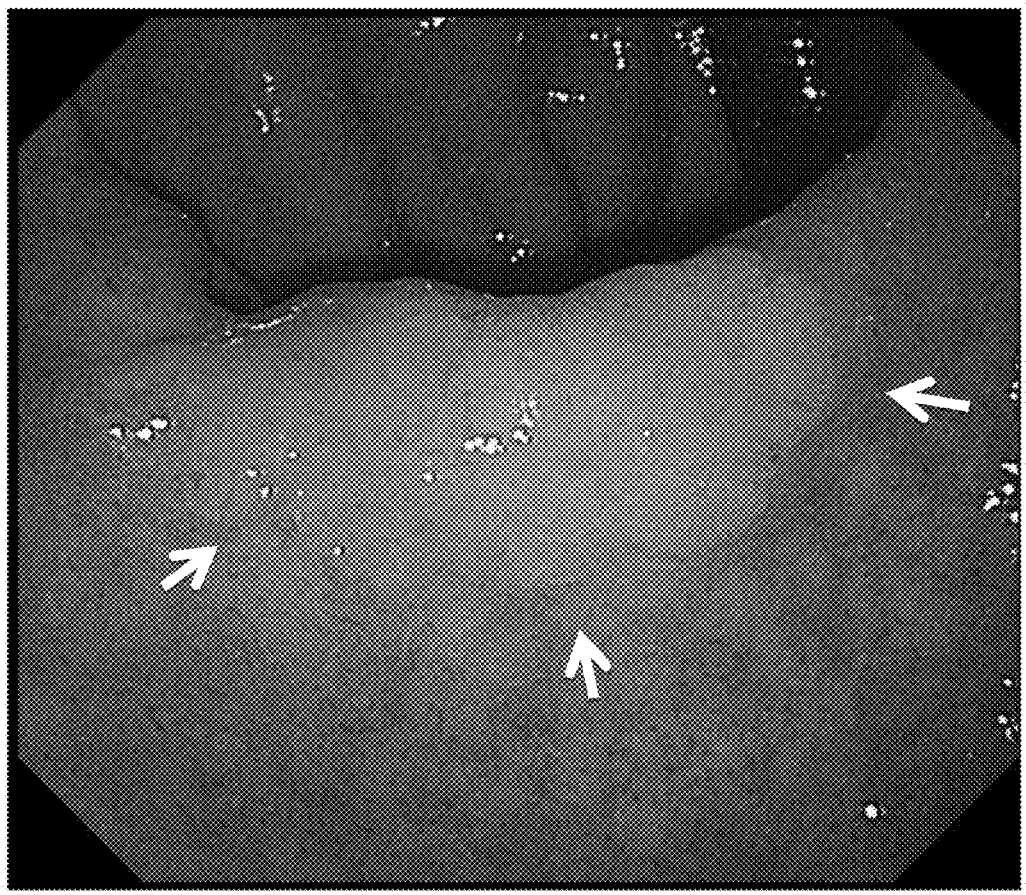
FIG. 16 shows an ordinary endoscopic image of carcinoma in a patient with gastric carcinoma of elevated type.

9. Endoscopic images and pathological photo of a subject with gastric carcinoma of elevated type:

(1) FIG. 16 shows an ordinary endoscopic image of a subject with gastric carcinoma of elevated type. Carcinoma with white color can be confirmed as indicated by arrows.

Figure 17:
FIG. 17 shows a NBI-combined magnifying endoscopic image of a border of carcinoma in a patient with gastric carcinoma of elevated type.

(2) FIG. 17 shows a NBI-combined magnifying endoscopic image of a border area of gastric carcinoma. Arrows show a border between gastric neoplasia and the normal part. The subepithelial microvessels can be confirmed on the left side of the border area, however, the WOS having irregular morphology are deposited on the right side in the epithelium, and accordingly the subepithelial blood vessels cannot be observed.

Figure 18:
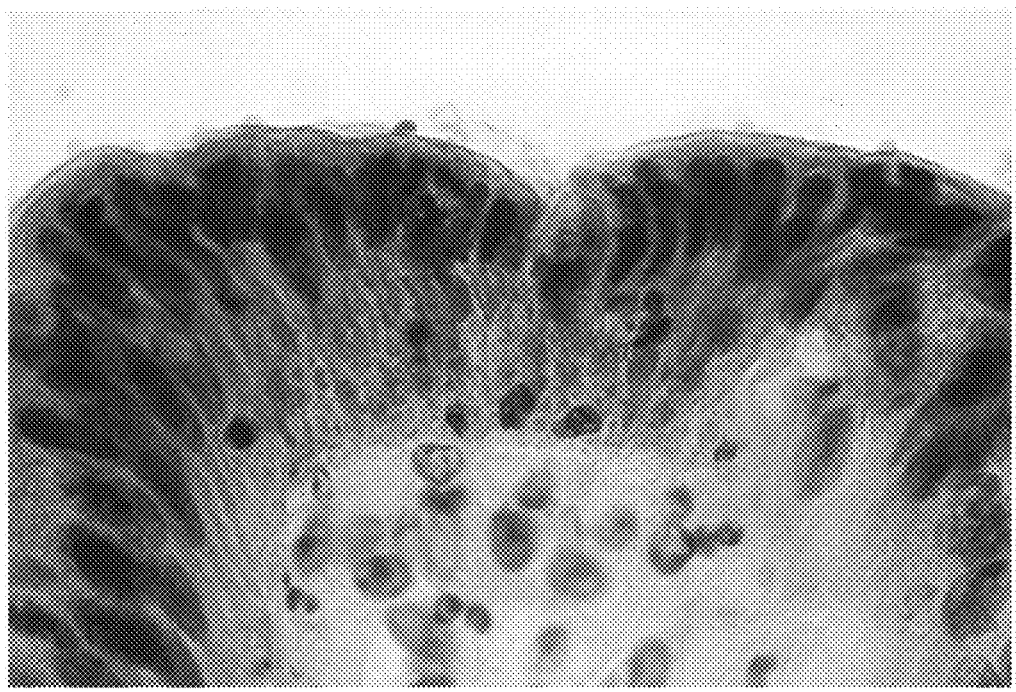
FIG. 18 shows an ORO staining image of a biopsy specimen collected from gastric neoplasia part of carcinoma in a patient with gastric carcinoma of elevated type.

(3) FIG. 18 shows histopathological findings (ORO staining) of a biopsy specimen collected from gastric carcinoma.

The ORO staining revealed that a large number of minute fat droplets absorbed and accumulated are present within the epithelium.

Figure 19:
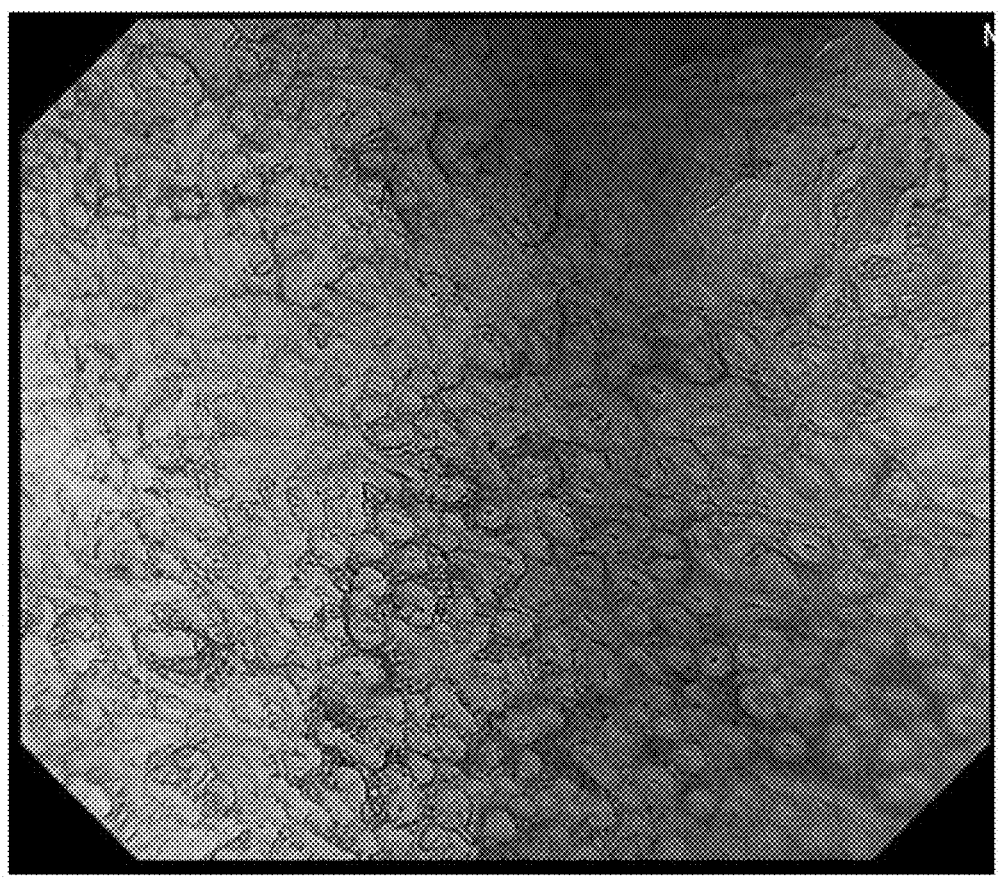
FIG. 19 shows a NBI-combined magnifying endoscopic image of gastritis in a patient with chronic gastritis.

10. Endoscopic and pathological images of a subject with chronic gastritis:

(1) FIG. 19 shows a NBI-combined magnifying endoscopic image of a subject with chronic gastritis. Subepithelial blood vessels are clearly visualized in brown, and there is no opaque substance within the epithelium, that is, a WOS is absent.

Figure 20:
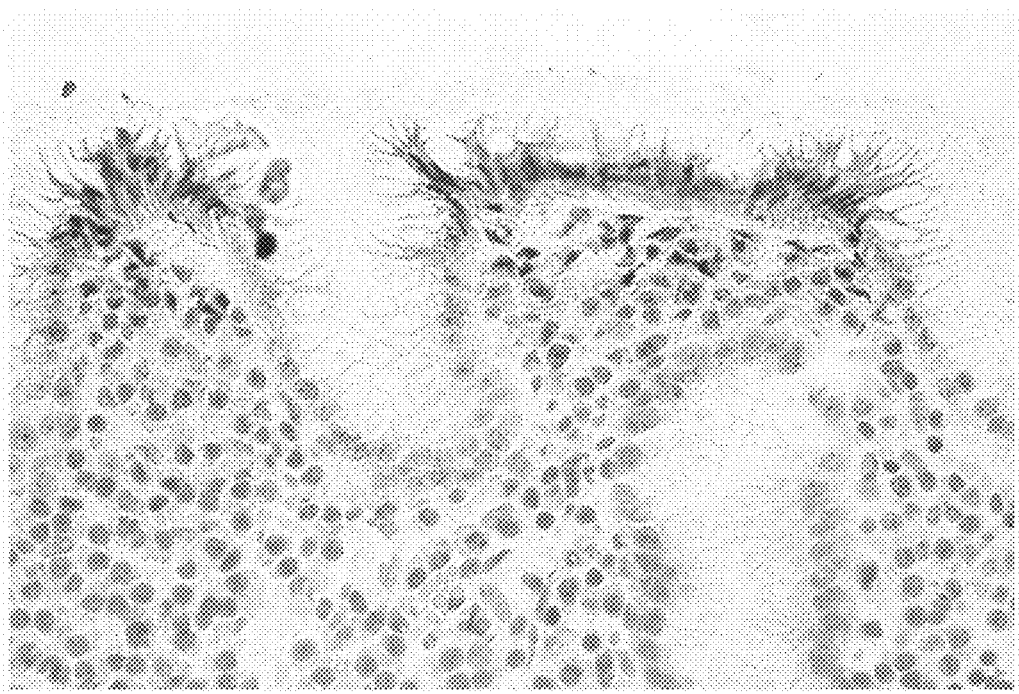
FIG. 20 shows an ORO staining image of a biopsy specimen obtained from gastritis mucosa of a patient with chronic gastritis.

(2) FIG. 20 shows histopathological findings (ORO staining) of a biopsy specimen collected from gastritis. It is confirmed by the ORO staining that there are no fat droplets within the epithelium or underneath the epithelium.

The invention claimed is:

1. A method for the detection of gastric neoplasia in a patient, comprising:

administering or loading a composition to the patient orally, intraluminally by a tube, or endoscopically, said composition being in a liquid form and comprising a lipid selected from one or more than one of a simple lipid, a compound lipid and a derived lipid, said lipid being in a form of micelles which are composed of a bile acid, a monoglyceride, a fatty acid, a phospholipid selected from a group consisting of phosphatidic acid, biphosphatidic acid, lecithin, cephalin, phosphatidyl ethanolamine, phosphatidyl methylethanolamine, phosphatidylserine, phosphatidylinositol, phosphatidyldycerin, disphosphatidylglycerin and sterol, wherein, if the patient has the gastric neoplasia, the lipid of the composition is absorbed into epithelial cells of the gastric neoplasia in the patient accumulating and forming the lipid of the composition to fat droplets which are visualized as white opaque substance accumulation in the epithelial cells thereof;

carrying out endoscopic examination to detect said fat droplets of the white opaque substance accumulation in the epithelial cells of the gastric neoplasia; and performing a morphological analysis for said fat droplets of the white opaque substance accumulation detected in the epithelial cells of the gastric neoplasia by the endoscopic examination to determine a morphological state of the gastric neoplasia.

2. The method according to claim 1, wherein endoscopic examination is carried out via NBI-combined magnifying endoscopy.

3. The method according to claim 1, wherein said morphological analysis includes observation of the morphological state of the fat droplets of the white opaque substance accumulation as to whether it is symmetrical or asymmetrical and determination that a symmetrical morphological state is a benign neoplasia and an asymmetrical morphological state is a malignant neoplasia.

4. The method according to claim 2, wherein said NBI-combined magnifying endoscopy is carried out for detecting or visualizing a pattern of minute blood vessels whose detection or visualization is obstructed by the presence of the fat droplets of the white opaque substance in a lesion detected by ordinary endoscopy without magnification.

* * * * *